United States Patent
Dasbach

(10) Patent No.: US 9,283,328 B2
(45) Date of Patent: Mar. 15, 2016

(54) NEEDLE ASSEMBLY ATTACHMENT AND REMOVAL DEVICE

(75) Inventor: Uwe Dasbach, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 129 days.

(21) Appl. No.: 14/128,024

(22) PCT Filed: Jun. 26, 2012

(86) PCT No.: PCT/EP2012/062282
§ 371 (c)(1),
(2), (4) Date: Dec. 20, 2013

(87) PCT Pub. No.: WO2013/000877
PCT Pub. Date: Jan. 3, 2013

(65) Prior Publication Data
US 2014/0123479 A1 May 8, 2014

(30) Foreign Application Priority Data
Jun. 28, 2011 (EP) .................................. 11171618

(51) Int. Cl.
*A61M 5/32* (2006.01)
*A61M 5/34* (2006.01)

(52) U.S. Cl.
CPC ............. *A61M 5/3276* (2013.01); *A61M 5/347* (2013.01); *Y10T 29/53* (2015.01)

(58) Field of Classification Search
CPC . A61M 5/3276; A61M 5/347; A61M 5/3202; A61M 5/3205; A61M 5/344; A61M 5/32; Y10T 29/53; Y10T 29/53339
See application file for complete search history.

(56) References Cited

U.S. PATENT DOCUMENTS

| 4,989,307 A * | 2/1991 | Sharpe et al. .................. 29/240 |
| 5,312,346 A | 5/1994 | Han |
| 2005/0236289 A1* | 10/2005 | Tanaka et al. ................. 206/366 |
| 2009/0069753 A1 | 3/2009 | Ruan et al. |

FOREIGN PATENT DOCUMENTS

| EP | 0903158 | 3/1999 |
| EP | 1567215 | 8/2005 |
| WO | 2004/047883 | 6/2004 |
| WO | 2010/023488 | 3/2010 |

OTHER PUBLICATIONS

International Search Report for Int. App. No. PCT/EP2012/062282, completed Aug. 23, 2012.

* cited by examiner

*Primary Examiner* — David Bryant
*Assistant Examiner* — Jun Yoo
(74) *Attorney, Agent, or Firm* — Fish & Richardson P.C.

(57) ABSTRACT

Described is a needle assembly attachment and removal device comprising of a base, an outer member fixed to the base, and a first inner member telescoped in the outer member. The outer member includes an inner surface of having first threads. The first inner member includes pins adapted to engage the first threads. The first inner member is adapted to hold a needle assembly. Axial movement of the first inner member within the outer member causes rotation of the first inner member and the needle assembly relative to the outer member.

13 Claims, 5 Drawing Sheets

NEEDLE ASSEMBLY ATTACHMENT AND REMOVAL DEVICE

CROSS REFERENCE TO RELATED APPLICATIONS

The present application is a U.S. National Phase Application pursuant to 35 U.S.C. §371 of International Application No. PCT/EP2012/062282 filed Jun. 26, 2012, which claims priority to European Patent Application No. 11171618.9 filed Jun. 28, 2011. The entire disclosure contents of these applications are herewith incorporated by reference into the present application.

TECHNICAL FIELD

The invention relates to a needle assembly attachment and removal device for attaching a needle assembly to and removing the needle assembly from a medicament delivery device.

BACKGROUND

Administering a medicament by injection is a process which presents a number of risks and challenges for patients and healthcare professionals, both mental and physical. Improper handling of medicament delivery devices may result in needle stick injuries. EP 0 903 158 B1, US 2009/0069753, and EP 1 567 215 discuss devices for coupling a needle assembly to a medicament delivery device. However, in any situation in which a patient or healthcare professional is required to manually attach/remove the needle assembly, there is a risk of needle stick injury.

In addition, manually attaching the needle assembly to the medicament delivery device can lead to over-tightening, which can result in injury when removing the needle assembly and/or structural damage to the medicament delivery device. Attempts to remove an over-tightened needle assembly can adversely affect other components of the medicament delivery device (e.g., in a reusable device, a cartridge holder may be loosened).

Thus, there is a need for a device for safely attaching and removing a needle assembly to/from a medicament delivery device.

SUMMARY

It is an object of the present invention to provide a needle assembly attachment and removal device for attaching a needle assembly to and removing the needle assembly from a medicament delivery device.

The object is achieved by a needle assembly attachment and removal device for attaching a needle assembly to and removing the needle assembly from a medicament delivery device according to claim 1.

In an exemplary embodiment, a needle assembly attachment and removal device comprising a base, an outer member fixed to the base, and a first inner member telescoped in the outer member. The outer member includes an inner surface of having first threads. The first inner member includes pins adapted to engage the first threads. The first inner member is adapted to hold a needle assembly. Axial movement of the first inner member within the outer member causes rotation of the first inner member and the needle assembly relative to the outer member.

In an exemplary embodiment, the outer member includes a proximal opening adapted to receive a medicament delivery device. The outer member may include one or more guides adapted to align the medicament delivery device with the proximal opening.

In an exemplary embodiment, the first inner member includes a cavity adapted to hold a cap for the needle assembly. The cavity may include one or more splines adapted to prevent rotation of the cap relative to the first inner member.

In an exemplary embodiment, the outer member includes a proximal section and a distal section. The distal section may have a larger diameter than the proximal section. The distal section and the outer member may have substantially a same diameter. The outer member may include a shoulder formed between the proximal section and the distal section. A portion of an internal face of the shoulder may include a first ratchet face. A second inner member may be disposed in the outer member and adapted to receive the first inner member. An inner surface of the second inner member may have second threads adapted to engage the pins.

In an exemplary embodiment, the second inner member includes a second ratchet face adapted to engage the first ratchet face. The second inner member is adapted to rotate relative to the outer member from a first position in which the second threads are aligned with the first threads and a second position in which the second threads are not aligned with the first threads. At least one of an audible feedback and a tactile feedback may be provided upon rotation of the second inner member relative to the outer member. When the first inner member is received in the second inner member, the axial movement of the first inner member may result in an axial force and a rotational force on the second inner member when the pins abut the second threads. The first inner member may be prevented from axial movement relative to the second inner member when the second inner member is in the second position.

In an exemplary embodiment, a first spring may be grounded in the base and bias the first inner member away from the base. A second spring may be grounded in the base and bias the second inner member away from the base, maintaining engagement of the first ratchet face and the second ratchet face.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
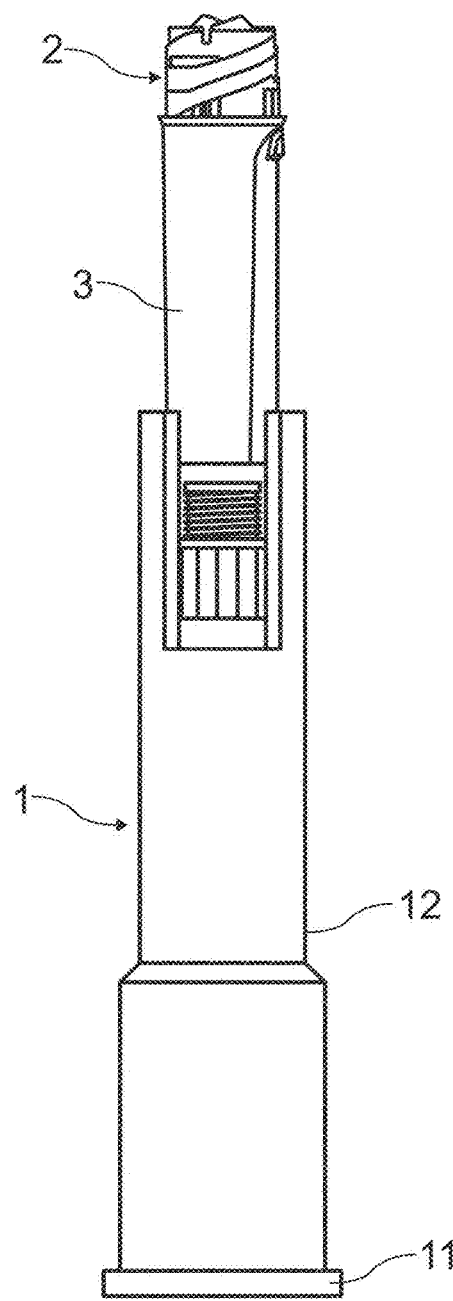
FIG. 1 is a lateral view of a needle assembly attachment and removal device according to an exemplary embodiment of the present invention.

FIG. 1 is a lateral view of an exemplary embodiment a needle assembly attachment and removal device 1 according to an exemplary embodiment of the present invention. The device 1 is adapted to receive a medicament delivery device 2 and to attach and remove a needle assembly 6 to/from the delivery device 2.

In an exemplary embodiment, the delivery device 2 includes a cartridge holder 3 adapted to hold a medicament-containing cartridge 4. The cartridge holder 3 may be cylindrical. The delivery device 2 may be any medicament delivery device including, but not limited to, a pen injector, an auto-injector, a safety syringe, etc.

As shown in FIG. 1, an exemplary embodiment of the device 1 includes an outer member 12 coupled to a base 11. In an exemplary embodiment, the outer member 12 is cylindrical and is adapted to receive the delivery device 2.

Figure 2:
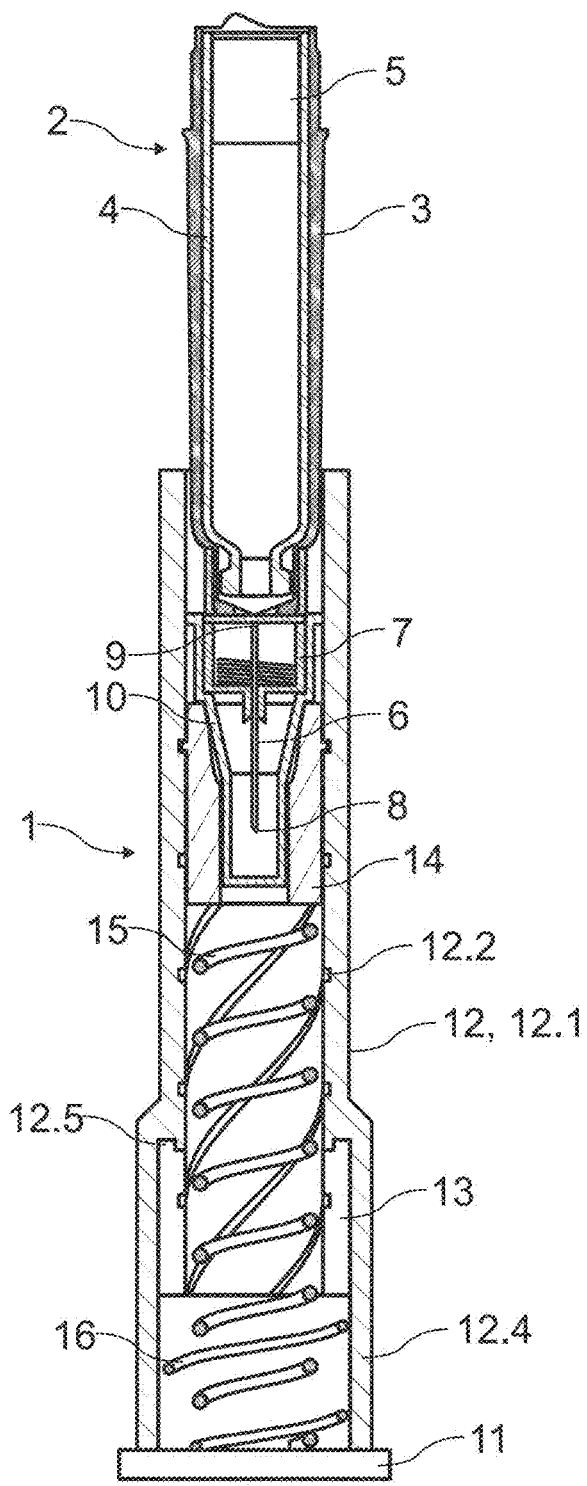
FIG. 2 is a longitudinal section of a needle assembly attachment and removal device according to an exemplary embodiment of the present invention.

FIG. 2 shows an exemplary embodiment of the device 1 according to the present invention. The cartridge 4 may comprise a cylindrical wall defining a cavity within. A stopper 5 may be axially movable with the cavity to discharge a medicament therein. As understood by those of skill in the art, the delivery device 2 may be a single-use device (e.g., the delivery device 2 is disposed of after the cartridge is empty) or a re-usable device (e.g., the cartridge 4 may be replaced when empty or otherwise necessary). A distal end of the cartridge includes a septum and an adapter for mounting the needle assembly 6. The needle assembly 6 includes a needle hub 7 and a needle which has a distal tip 8 and a proximal tip 9. The proximal tip 9 is arranged to pierce the septum when the needle assembly 6 is mounted to the cartridge 4, and the distal tip 8 is used to pierce an injection site. When the needle assembly 6 is coupled to the delivery device 2, the medicament can be displaced through a fluid channel within the needle. In an exemplary embodiment, the needle hub 7 includes internal threads for mating with threads formed on the cartridge 4 or the cartridge holder 3.

Prior to use, the needle assembly 6 may be surrounded by a cap 10 for maintaining sterility of the needle assembly and preventing damage to the needle and needle stick injuries. In order to prepare the delivery device 2 for an injection, the needle assembly 6 is mounted to the delivery device 2 and removed from the cap 10.

As shown in FIG. 2, in an exemplary embodiment the device 1 includes the outer member 12 coupled to the base 11, a first inner member 14, a second inner member 13, a first spring 15 and a second spring 16. In an exemplary embodiment, a distal end of the outer member 12 may be fixed to a proximal side of the base 11. The outer member 12 may include an ergonomic gripping surface for allowing a user to hold the device 1 in one hand when attaching/removing the needle assembly 6. In an exemplary embodiment, the base 11 may be adapted for placing the device 1 on a flat surface such as a table or desk. For example, the base 11 may have a significantly larger cross-section than the outer member 12 to enhance stability during use of the device 1. A distal side of the base 11 may include an adhesive or a suction device. In another exemplary embodiment, a coupling device (e.g., a vice) may be secured to a surface, and the coupling device may include an interface for lockingly engaging the base 11 of the device 1.

Figure 3:
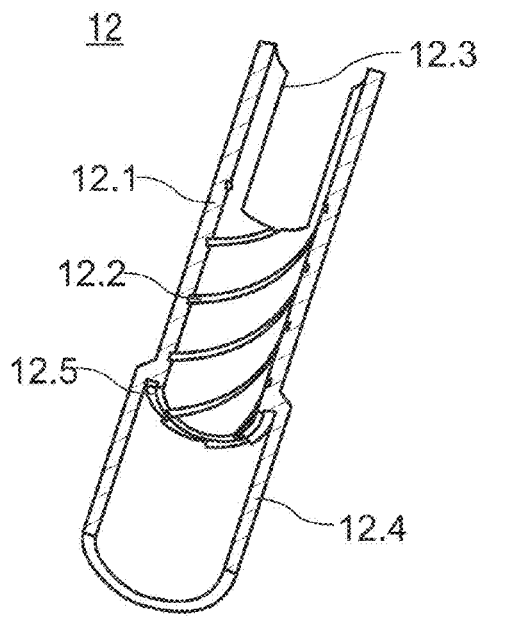
FIG. 3 is a perspective longitudinal section of an outer member of a needle assembly attachment and removal device according to an exemplary embodiment of the present invention.
Figure 4:
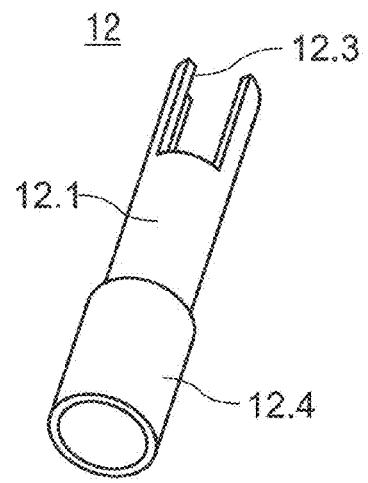
FIG. 4 is a perspective longitudinal view of the outer member of a needle assembly attachment and removal device according to an exemplary embodiment of the present invention.

FIGS. 3 and 4 show an exemplary embodiment of the outer member 12 according to the present invention. In an exemplary embodiment, the outer member 12 is cylindrical, but those of skill in the art will understand that other geometries are possible. The outer member 12 includes a proximal section 12.1 and a distal section 12.4. In an exemplary embodiment, the proximal section 12.1 is cylindrical and has a first diameter, and the distal section 12.4 is cylindrical and has a second diameter, larger than the first diameter. The proximal section 12.1 may include one or more first threads 12.2 formed along at least a member of its length. In an exemplary embodiment, an internal shoulder is defined between the proximal section 12.1 and the distal section 12.4. A portion of the shoulder may be arranged as a first ratchet face 12.5 comprising a set of ratchet teeth arranged along a circumference of the shoulder.

In an exemplary embodiment, one or more guides 12.3 may project proximally from the proximal section 12.1. The guides 12.3 may be adapted to align the delivery device 3 within the outer member 12 when the delivery device 1 is engaging or disengaging a needle assembly 6. For example, the guides 12.3 may be formed by removing cut-outs from an extension of the proximal section 12.1.

Figure 5:
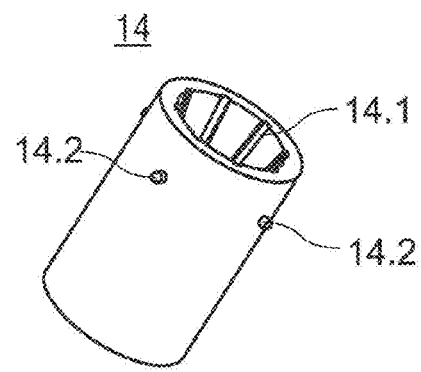
FIG. 5 is a perspective view of a first inner member of a needle assembly attachment and removal device according to an exemplary embodiment of the present invention.

FIG. 5 is a perspective view of an exemplary embodiment of the first inner member 14. In an exemplary embodiment, the first inner member 14 is a tube-shaped member which has a cavity with an inner surface adapted to receive the cap 10 for the needle assembly 6. The inner surface may include splines 14.1 which may engage grooves (or corresponding splines) on the cap 10 to prevent rotation of the cap 10 relative to the needle assembly 6. An outer surface of the first inner member 14 may include pins 14.2 for engaging the first threads 12.2 of the outer member 12 when telescoped in the proximal section 12.1.

Figure 6:
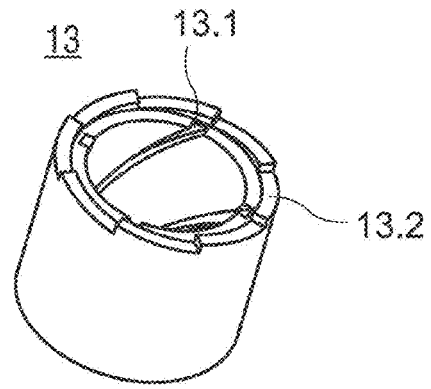
FIG. 6 is a perspective view of a second inner member of a needle assembly attachment and removal device according to an exemplary embodiment of the present invention.

FIG. 6 is a perspective view of an exemplary embodiment of the second inner member 13. In an exemplary embodiment, the second inner member 13 is a tube-shaped member telescoped in the distal section 12.4 of the outer member 12 and adapted to receive the first inner member 14. The second inner member 13 has one or more second threads 13.1 formed on its inner surface. The second threads 13.1 may have the same pitch as the first threads 12.2 such that when the second threads 13.1 are aligned with the first threads 12.2, a continuous spiral is formed. The second threads 13.1 may extend through only a portion of the length of the second inner member 13. A proximal end of the second inner member 13 may include a second ratchet face 13.2 comprising a set of ratchet teeth arranged along its circumference. The second ratchet face 13.2 is adapted to engage the first ratchet face 12.5 of the outer member 12.

In an exemplary embodiment, the engagement of the first and second ratchet faces 12.5, 13.2 may be arranged such that rotation of the second inner member 13 relative to the outer member 12 may be limited to one rotational direction. Further, the rotation of the second inner member 13 relative to the outer member 12 may occur in a step rotation such that in a first position (an aligned position) the first and second threads 12.2 and 13.1 may be aligned. And, after a first step rotation, the first and second threads 12.2 and 13.1 may be in a second position (a misaligned position), and, the first and second threads 12.2 and 13.1 may be misaligned. Thus, in the aligned position, the first inner member 14 may travel between the proximal portion 12.1 of the device 1 and the second inner member 13, and in the misaligned position, the first inner member 14 may be restricted to the distal portion 12.4 of the device 1 or the second inner member 13 because the pins 14.2 may abut a rim formed on a distal end of the proximal portion 12 (internal to first ratchet face 12.5) or a rim formed on a proximal end of the second inner member 13 (internal to the second ratchet face 13.2).

Referring back to FIG. 2, in an exemplary embodiment, the first spring 15 is grounded in the base 11 and bears against the first inner member 14 thereby biasing it away from the base 11. In an exemplary embodiment, the second spring 16 has a greater diameter than the first spring 15, and the second spring 16 is grounded in the base 11 and bears against the second inner member 13 thereby biasing it away from the base 11 and keeping the ratchet faces 13.2, 12.5 engaged.

FIG. 2 shows an exemplary embodiment of the device 1 prior to use. In this exemplary embodiment, the device 1 includes an unused needle assembly 6 contained in the cap 10. In an exemplary embodiment, an opening in the cap 10 may be covered with a peelable film which is removed prior to use of the device 1. In an exemplary embodiment, after a used needle assembly 6 has been deposited in the device 1, the device 1 may be discarded, or the used needle assembly 6 (and corresponding cap 10) may be discarded and an unused needle assembly 6 may be deposited in the device 1. For example, as shown in FIG. 2, a portion of the cap 10 extends beyond the first inner member 14, and spaces between the guides 12.3 provide access to the cap 10 for removal and replacement of the used needle assembly 6.

For the delivery device 2 to engage the unused needle assembly 6, the delivery device 2 is aligned with the device 1 using the guides 12.3. The cartridge holder 3 is inserted into the needle hub 7, and a distally directed force is applied. As the delivery device 2 is advance distally into the device 1, the first inner member 14 moves axially within the proximal section 12.1 against the force of the first spring 15. The engagement of the pins 14.2 in the first threads 12.2 causes the first inner member 14 to rotate in a first rotational direction relative to the device 1 as the first inner member 14 moves distally. Rotation of the first inner member 14 in the first rotational direction results in rotation of the cap 10, and thereby engagement, of the needle assembly 6 to the delivery device 2 (because the needle assembly 6 does not rotate relative to the cap 10).

Figure 7:
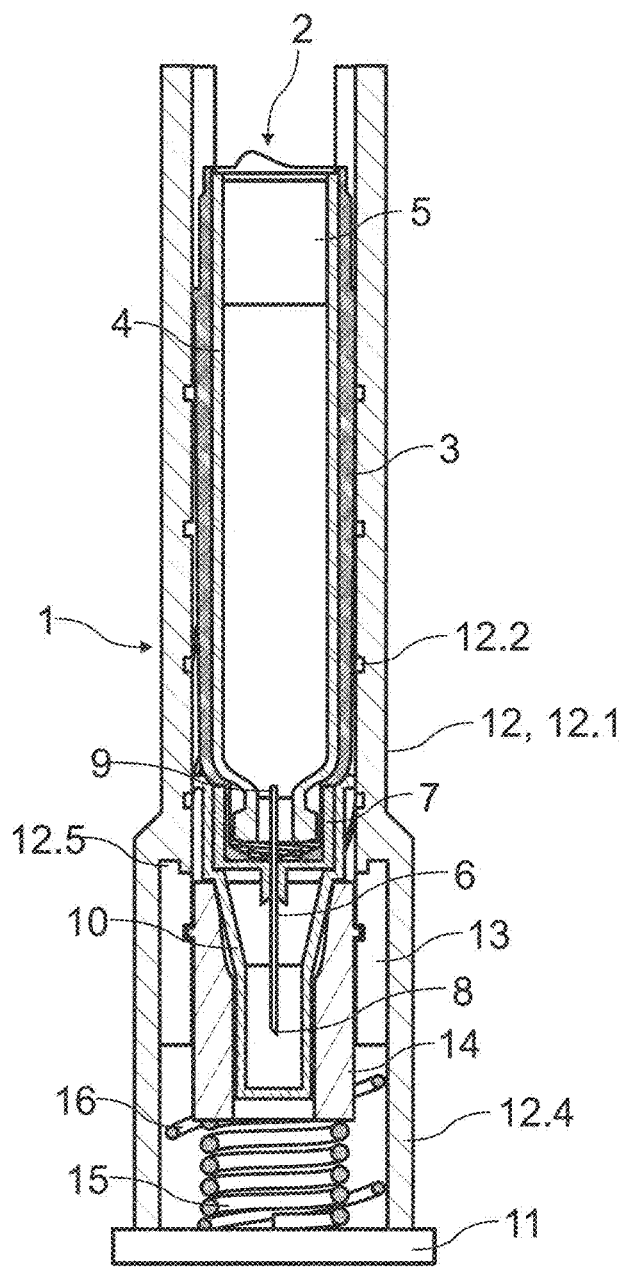
FIG. 7 is a longitudinal section of a needle assembly attachment and removal device during an attachment operation according to an exemplary embodiment of the present invention.

As shown in the exemplary embodiment in FIG. 7, because the first and second threads 12.2 and 13.1 are in the aligned position, the first inner member 14 continues to moves distally and into the second inner member 13 when it reaches the shoulder between the proximal section 12 and the distal section 12.4. When the needle assembly 6 has been properly secured to the delivery device 2, the first inner member 14 will encounter some resistance upon continued rotation. That is, if the delivery device 2 is held in a static orientation relative to the device 1, after the needle assembly 6 has been secured to the delivery device 2, the first inner member 14 may be hindered from further rotation relative to the second inner member 13. As such, further distally directed force applied to the delivery device 2 may cause the pins 14.2 to abut the second thread 13.1, transmitting a distally directed force to the second inner member 13. Thus, as the delivery device 2 is advanced further into device 1, the first inner member 14 is compressed against the force of the second spring 16 separating the first and second ratchet faces 12.5 and 13.2. Separation of the first and second ratchet faces 12.5 and 13.2 may provide a tactile feedback (e.g., the user may begin to feel the device 2 attempting to rotate with the first inner member 14), and in another exemplary embodiment, an audible feedback (e.g., a click) may be provided so that the user knows that the needle assembly 6 is secured to the delivery device 2 (as opposed to e.g., that the delivery device 2 is stuck in the device 1).

Figure 8:
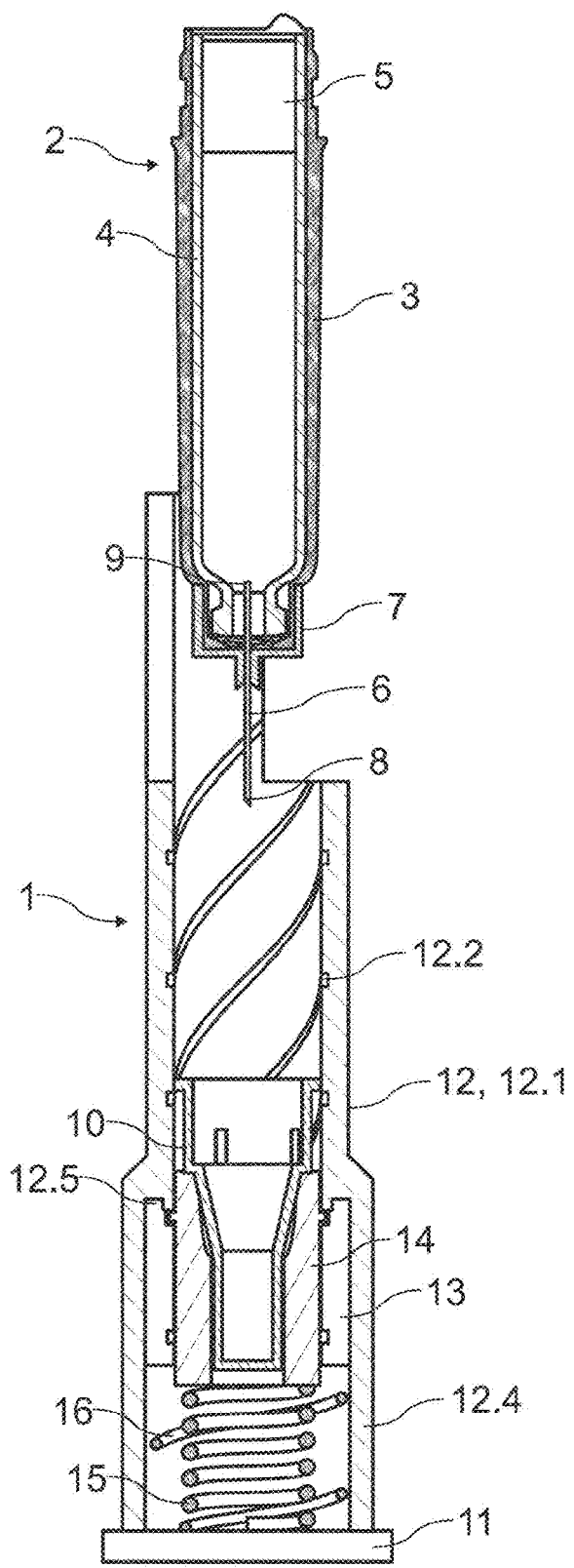
FIG. 8 is a longitudinal section of a needle assembly attachment and removal device after an attachment operation according to an exemplary embodiment of the present invention.

As shown in the exemplary embodiment in FIG. 8, when axial force (in the distal direction) is released from the delivery device 2, the second spring 16 causes the second inner member 13 to move proximally within the distal section 12, thereby causing the re-engagement of the first and second ratchet faces 12.5 and 13.2. Due to the rotation of the second inner member 13 relative to the device 1, the first threads 12.1 of the proximal section 12 and the second threads 13.1 of the second inner member 13 are in the misaligned position. Thus, when the first spring 15 forces the first inner member 14 proximally, the pins 14.2 abut a portion of the shoulder 12.5 and prevent further proximal movement of the first inner member 14 relative to the device 1. The delivery device 2, with the needle assembly 6 engaged thereto, can then be withdrawn from the device 1 for administering an injection.

In an exemplary embodiment, after the medicament is delivered, the delivery device 2 can be reinserted into the device 1 to remove the used needle assembly 6.

When the delivery device 2 is inserted into the device 1, the used needle assembly 6 will abut the cap 10, forcing the first inner member 14 in the distal direction against the first spring 15. Movement of the first inner member 14 in the distal direction also causes the second inner member 13 to move in the distal direction, separating the first and second ratchet faces 12.5 and 13.2 and rotating the second inner member 13 (and first inner member 14 therewith) relative to the device 1. Rotation of the second inner member 13 (and first inner member 14 therewith) relative to the device 1 causes the first and second threads 12.1 and 13.1 to be in the aligned position. The first spring 15 may then drive the first inner member 14 axially proximally, which causes rotation of the first inner member 14 (and cap 10 and needle assembly 6 therewith) in a second rotational direction, disengaging the needle assembly 6 from the delivery device 1. The used needle assembly 6 may then be maintained in the cap 10 for being discarded, or the device 1 (with the used needle assembly 6 therein) may be discarded.

In an exemplary embodiment, the first spring 15 and the second spring 16 are arranged as linear compression springs. However, other springs may be used.

The sense of rotation defined by the first and second threads 12.2, 13.1 and the ratchet faces 12.5, 13.2 illustrated in the figures was chosen by way of example in order to allow screwing a right hand threaded needle hub 7 onto the right hand threaded adapter of the cartridge holder 3. It goes without saying that the sense of rotation could be the opposite by respectively modifying the first and second threads 12.2, 13.1 and the ratchet faces 12.5, 13.2 for screwing a left hand threaded needle hub 7 onto a left hand threaded cartridge holder 3.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle assembly attachment and removal device comprising:
    a base;
    an outer member fixed to the base, an inner surface of the outer member having first threads;
    a first inner member telescoped in the outer member and having pins adapted to engage the first threads, wherein the first inner member is adapted to hold a needle assembly; and
    a second inner member disposed in the outer member and adapted to receive the first inner member, an inner surface of the second inner member having second threads adapted to engage the pins,
    wherein axial movement of the first inner member within the outer member causes rotation of the first inner member and the needle assembly relative to the outer member.

2. The needle assembly attachment and removal device according to claim 1, wherein the outer member includes a proximal opening adapted to receive a medicament delivery device.

3. The needle assembly attachment and removal device according to claim 2, wherein the outer member includes one or more guides adapted to align the medicament delivery device with the proximal opening.

4. The needle assembly attachment and removal device according to claim 1, wherein the first inner member includes a cavity adapted to hold a cap for the needle assembly, wherein the cavity includes one or more splines adapted to prevent rotation of the cap relative to the first inner member.

5. The needle assembly attachment and removal device according to claim 1, wherein the outer member includes a proximal section and a distal section, and wherein the distal section has a larger diameter than the proximal section, and wherein the distal section and the outer member have substantially a same diameter.

6. The needle assembly attachment and removal device according to claim 5, wherein the outer member includes a shoulder formed between the proximal section and the distal section, wherein a portion of an internal face of the shoulder includes a first ratchet face.

7. The needle assembly attachment and removal device according to claim 1, wherein the second inner member includes a second ratchet face adapted to engage the first ratchet face.

8. The needle assembly attachment and removal device according to claim 7, wherein the second inner member is adapted to rotate relative to the outer member from a first position in which the second threads are aligned with the first threads and a second position in which the second threads are not aligned with the first threads.

9. The needle assembly attachment and removal device according to claim 8, wherein, at least one of an audible feedback and a tactile feedback is provided upon rotation of the second inner member relative to the outer member.

10. The needle assembly attachment and removal device according to claim 8, wherein, when the first inner member is received in the second inner member, the axial movement of the first inner member results in an axial force and a rotational force on the second inner member when the pins abut the second threads.

11. The needle assembly attachment and removal device according to claim 8, wherein the first inner member is prevented from axial movement relative to the second inner member when the second inner member is in the second position.

12. The needle assembly attachment and removal device according to claim 1, further including:
    a first spring grounded in the base and biasing the first inner member away from the base.

13. The needle assembly attachment and removal device according to claim 7, further including:
    a second spring grounded in the base and biasing the second inner member away from the base and maintaining engagement of the first ratchet face and the second ratchet face.

* * * * *